United States Patent [19]

Bosman et al.

[11] Patent Number: 5,227,028

[45] Date of Patent: Jul. 13, 1993

[54] PROCESS FOR TREATING AMIDES

[75] Inventors: Hubertus J. M. Bosman, Sittard; Paul C. Van Geem, Schinnen, both of Netherlands; Petrus J. H. Thomissen, Lanaken, Belgium

[73] Assignee: DSM N.V., Heerlen, Netherlands

[21] Appl. No.: 725,090

[22] Filed: Jul. 3, 1991

[30] Foreign Application Priority Data

Jul. 6, 1990 [NL] Netherlands .................... 9001545

[51] Int. Cl.$^5$ .................. B01D 3/34; C07D 201/16
[52] U.S. Cl. .................................. 203/29; 203/34; 203/35; 203/38; 540/485; 540/540
[58] Field of Search ............... 203/29, 35, 34, 38; 540/540, 485

[56] References Cited

U.S. PATENT DOCUMENTS

| 3,016,376 | 1/1962 | Francis | 540/540 |
| 3,248,388 | 4/1966 | Wintersberger et al. | 203/35 |
| 3,288,687 | 11/1966 | Zimmerli et al. | 203/35 |
| 4,349,520 | 9/1982 | Bonfield et al. | 423/387 |

FOREIGN PATENT DOCUMENTS

| 47-30680 | 11/1972 | Japan | 540/540 |
| 57-24357 | 2/1982 | Japan | 540/540 |
| 57-209269 | 12/1982 | Japan | 540/540 |
| 168705 | 2/1965 | U.S.S.R. | 540/540 |
| 595305 | 2/1978 | U.S.S.R. | 540/540 |
| 1286427 | 8/1972 | United Kingdom . | |

OTHER PUBLICATIONS

"Aliphatic Compounds", vol. 63, 1965, Col. 1709, Section C.
Chemical Abstracts, vol. 93, 1980, Section 93 150693n, p. 2.

*Primary Examiner*—Wilbur Bascomb, Jr.

[57] ABSTRACT

A process of treating a ketoxime or aldoxime-containing amide mixture resulting from a Beckmann rearrangement of the corresponding ketoxime or aldoxime. The process involves hydrolysis of the mixture to remove the remaining ketoxime or aldoxime which are converted to the corresponding ketone or aldehyde and then separated off from the mixture. Any amino acid resulting from the hydrolysis can be reconverted to the corresponding amide by raising the temperature of the mixture.

14 Claims, No Drawings

PROCESS FOR TREATING AMIDES

FIELD OF INVENTION

The invention relates to a process treating a ketoxime or aldoxime-containing amide mixture obtained by a Beckmann rearrangement of the corresponding ketoxime or aldoxime.

BACKGROUND OF THE INVENTION

Such a process is known from GB-A-1286,427. In that patent publication a process is described for removing cyclohexanone oxime from caprolactam by supplying gaseous sulphur dioxide to and dissolving it in the cyclohexanone oxime-containing caprolactam mixture at a temperature of 70°-170° C., the sulphur dioxide being dissolved to a concentration of at least 1 mole sulphur dioxide per mole cyclohexanone oxime. After completion of the reaction of the sulphur dioxide with the remaining cyclohexanone oxime, the excess of sulphur dioxide is removed by evaporating it from the reaction mixture under reduced pressure or by supplying inert gases to the reaction mixture. The purified caprolactam is subsequently recovered by distillation.

A disadvantage of such a process is that the product formed by the reaction of sulphur dioxide with a ketoxime or aldoxime is a process-alien substance, which must therefore be removed from the process, so that a potential amount of amide to be formed, viz. the non-rearranged ketoxime or aldoxime, is withdrawn from the process.

It is generally known in the art how to produce amides, for instance lactams such as s-caprolactam, by means of a homogeneously catalytic Beckmann rearrangement of ketoximes or aldoximes such as, for instance, cyclohexanone oxime. This rearrangement is effected by treating the ketoxime or aldoxime with strong acids such as, for instance, sulphuric acid, oleum, chlorosulphonic acid, hydrogen fluoride, polyphosphoric acid, phosphorus pentachloride and the like. When using, for instance, sulphuric acid or oleum, a sulphuric acid-amide complex is obtained after the rearrangement, upon which the desired amide must be recovered by neutralizing the reaction mixture with usually ammonia water, in which process a large amount of ammonium sulphate is obtained as byproduct.

Another and more favorable process is the conversion of a ketoxime or aldoxime into the corresponding amide by means of a heterogeneously catalytic Beckmann rearrangement using a solid acid or neutral catalyst, for instance a rearrangement in the gas phase or in the liquid phase. Examples of a solid acid or neutral catalyst to be used are boric acid on a carrier, such as silica or alumina, and crystalline silicas, such as silicalite I (silicon-rich MFI (Mobil Five, also known as ZSM5)) and silicalite II (silicon-rich MEL (Mobil Eleven, also known as ZSM11)), as well as an acid ion exchanger or (mixed) metal oxides and the like. An advantage is that in such a process no ammonium sulphate is formed as byproduct.

In such Beckmann rearrangement processes, however, an incomplete conversion of the ketoxime or aldoxime may occur, causing a certain amount of non-reacted ketoxime or aldoxime to leave the reactor along with the amide formed. On the other hand, a complete removal of the ketoxime or aldoxime from the oxime-containing amide mixture is highly desirable in order to obtain a high degree of amide purity in the preparation of the amide and in order to avoid disturbances in the further amide preparation process. Now, the separation of this oxime from the oxime-containing amide mixture by means of physical separation techniques is very difficult and can be realized only at high costs (reference may be made to GB-A-1,286,427).

SUMMARY OF THE INVENTION

The object of the invention is to provide a simpler process that does not yield process-alien material as reaction product.

This object is achieved according to the process of the present invention in that the ketoxime or aldoxime-containing amide mixture is subjected to a hydrolysis reaction.

A hydrolysis reaction is understood to mean in this connection a reaction in an aqueous medium known per se to the person skilled in the art. The ketoxime or aldoxime used is converted by it to form hydroxyl amine and the corresponding ketone or aldehyde.

DETAILED DESCRIPTION OF THE INVENTION

Examples of ketoximes or aldoximes in ketoxime or aldoxime-containing amide mixtures that can be treated according to the present invention and obtained from a Beckmann rearrangement, include saturated and unsaturated, substituted or non-substituted aliphatic ketoximes or aldoximes or cyclic ketoximes with 2-12 carbon atoms, such as acetone oxime, acetaldoxime, benzaldoxime, propanal oxime, butanal oxime, butanone oxime, butene1-one oxime, cyclopropanone oxime, cyclohexanone oxime, cyclooctanone oxime, cyclododecanone oxime, cyclopentanone oxime, cyclododecenone oxime, 2-phenylcyclohexanone oxime, cyclohexenone oxime.

According to the process of the present invention, the hydrolysis reaction is carried out under conditions sufficient to obtain an amide mixture which is substantially oxime-free. It has been found that good results can be achieved in the hydrolysis reaction with a temperature between 50° C. and 150° C. A more preferred temperature range would be between 80° C. and 120° C. Although the hydrolysis reaction may take place in a basic and neutral environment, this reaction preferably takes place in an acid environment.

The acid used is, for instance, a strongly mineral or organic acid, such as sulphuric acid, phosphoric acid, hydrochloric acid, nitric acid, trifluoro acetic acid, aromatic sulphonic acids, such as p-toluene sulphonic acid, or benzene sulphonic acid. Preference is given to the use of sulphuric acid, phosphoric acid or a mixture of these.

In the hydrolysis in an acid environment the pH is between 0 and 4 and preferably between 1.5 and 2.5. The pH is related here to the feed water.

The hydrolysis reaction may be carried out batchwise, as well as in a continuous process, and optionally in the presence of a heterogeneous catalyst. Preferably the heterogeneous catalyst is an acid cation exchanger. The heterogeneous catalyst can also be other than an acid cation exchanger, e.g. phosphoric acid absorbed on carbon black.

After the hydrolysis reaction, the amide that has been subjected to the treatment preferably has an oxime content no higher than 0.01% (wt), or 100 ppm.

It has been found that under the process conditions of the process according to the present invention that the rate of hydrolysis of the ketoxime or aldoxime is many times higher than the rate of hydrolysis of the corresponding amide. In the temperature range and in the pH range used for the invention the ratio of the relevant reaction-rate constants k(oxime)/k(amide) is higher than 10,000, depending on the amount of water used, so that the ketoxime or aldoxime can be hydrolysed almost completely without any appreciable conversion of the corresponding amide.

The amount of water to be used is not critical. The process according to the present invention requires an amount of water at least equivalent to the remaining oxime, and it is convenient to use an excess of water, for instance 10–100 equivalents.

The rearrangement of the ketoxime or aldoxime to form the corresponding amide can be carried out, if so desired, to a low degree of conversion, for instance a conversion of 75%.

Preference is given to a rearrangement with a conversion of at least 90% and more in particular with a conversion up to at least 95%.

Irrespective of the conversion percentage involved in the rearrangement, the resulting oxime hydrolysis products, viz. the corresponding alkanone or aldehyde and hydroxyl amine, can be separated off during or after the hydrolysis reaction in a manner known to the person skilled in the art, for instance by distillation. They can advantageously be returned to the oxime preparation process, also referred to as oximation, which precedes the rearrangement. In the process, loss of oxime is thus avoided.

The product of hydrolysis of converted amide, too, such as, for instance, ε-aminocaproic acid, which is obtained after hydrolysis of a caprolactam mixture containing cyclohexanone oxime, can be reconverted into the corresponding amide, for instance by raising the temperature.

This does not involve any loss of ketoxime or aldoxime, nor of amide, so that an optimum efficiency is achieved.

It should be noted that the hydrolysis of a ketoxime or aldoxime to form the corresponding alkanone or aldehyde and hydroxyl amine is described in U.S. Pat. No. 4,349,520. That patent publication, however, does not describe the hydrolysis of a ketoxime or aldoxime-containing amide mixture.

The invention will now be elucidated by means of the typical embodiments without, however, being limited hereto.

EXAMPLES

Example 1

To a stirred 15-liter reactor were continuously supplied at a temperature of 100° C. 0.1 kg/sec of a caprolactam mixture containing 30,000 ppm cyclohexanone oxime and 0.0'kg/sec phosphoric acid-containing water (10% by wt) calculated on the cyclohexanone oxime-containing caprolactam mixture) with a pH of 1.8, which materials were hydrolysed with a residence time of 100 seconds. The outflow still contained 417 ppm cyclohexanone oxime in the total caprolactam and 96.86% (wt) caprolactam in the anhydrous system, which meant that 98.6% of the cyclohexanone oxime present had been converted into hydroxyl amine and cyclohexanone. Also, only 0.14% of the caprolactam present had been converted into ε-aminocaproic acid. This caprolactam mixture, which still contained a small amount of cyclohexanone oxime, was hydrolysed once again under the same conditions in a second stirred 15-liter reactor. The outflow now contained only 5 ppm cyclohexanone oxime in the caprolactam and 96.7% (wt) caprolactam in the anhydrous system, which meant that 98.65% of the cyclohexanone oxime remaining in the feed and only 0.15% of the caprolactam had been converted in this second step. A total amount of 0.29% caprolactam had been converted into ε-aminocaproic acid. During its upgrading by distillation to purified caprolactam, this ε-aminocaproic acid was converted again into the same amount of caprolactam, so that there was no loss of product.

Example 2

Example 1 was repeated, however with the difference that this time the hydrolysis reaction was carried out at a temperature of 95° C. with 30% (wt) sulphuric acid-containing water in the cyclohexanone oxime-containing caprolactam mixture. The outflow from the second reactor contained only 10 ppm cyclohexanone oxime in the caprolactam. A total amount of 0.19% caprolactam had been converted into ε-aminocaproic acid.

Example 3

Example 1 was repeated, however with the difference that this time the hydrolysis reaction was carried out at a pH of 2 with 5% (wt) phosphoric acid-containing water in the cyclohexanone oxime-containing caprolactam mixture. The outflow from the second reactor contained only 25 ppm cyclohexanone oxime in the caprolactam. A total amount of 0.29% caprolactam had been converted into ε-aminocaproic acid, which was converted again into the same amount of caprolactam during the upgrading by distillation.

Example 4

Example 2 was repeated, however with the difference that this time the hydrolysis reaction was carried out at a pH of 2. The outflow from the second reactor contained only 40 ppm cyclohexanone oxime in the caprolactam. A total amount of 0.19% caprolactam had been converted into ε-aminocaproic acid.

Example 5

Example 1 was repeated, however with the difference that the hydrolysis reaction was carried out at a pH of 2.2 in a 75-liter reactor using 20% (wt) phosphoric acid-containing water in the cyclohexanone oxime-containing caprolactam mixture, with a residence time of 500 sec. The outflow contained only 3 ppm cyclohexanone oxime in the caprolactam. A total amount of 1.42% caprolactam had been converted into ε-aminocaproic acid, which was converted again into caprolactam during its upgrading by distillation.

Example 6

Example 2 was repeated, however with the difference that this time the hydrolysis reaction was carried out at a pH of 2.2 in a 75-liter reactor with a residence time of 500 sec. The outflow from the second reactor contained only 4 ppm cyclohexanone oxime in the caprolactam. A total amount of 0.95% caprolactam had been converted into ε-aminocaproic acid.

Example 7

To a packed column filled with 25 kg ion exchanger (Amberlist 15, a product of Rohm and Haas) was supplied 0.'kg/sec. of the caprolactam mixture of example I, together with 0.02 kg/sec. water. The reaction temperature was 100° C. The outflow contained only 8 ppm cyclohexanone oxime in the caprolactam. A total amount of 0.15% caprolactam had been converted into ε-aminocaproic acid.

Example 8

Example 1 was repeated so, however, that this time the hydrolysis reaction was carried out at a temperature of 95° C. with an N-methylacetamide mixture containing 30,000 ppm acetone oxime and 30% (wt) p-toluenesulphonic acid-containing water in the acetone oxime-containing N-methylacetamide mixture with a pH of 2. The outflow contained only 14 ppm acetone oxime in the N-methylacetamide. A total amount of 0.25% N-methylacetamide had been converted into formic acid and methylamine; during the upgrading of the hydrolysis mixture by distillation these were converted to form N-methylacetamide again.

Example 9

Example 1 was repeated so, however, that this time the hydrolysis reaction was carried out at a temperature of 100° C. using an N-ethylacetamide mixture containing 30,000 ppm 2-butanone oxime and 30% (wt) p-toluenesulphonic acid-containing water in the 2-butanone oxime-containing N-ethylacetamide mixture with a pH of 2. The outflow from the second reactor contained only 23 ppm 2-butanone oxime in the N-ethylacetamide. A total amount of 0.14% N-ethylacetamide had been converted into acetic acid and methyl amine.

Example 10

Example 1 was repeated so, however, that this time the hydrolysis reaction was carried out with a laurinolactam mixture containing 30,000 ppm cyclododecanone oxime and 30% (wt) phosphoric acid-containing water in a 75-liter reactor. The outflow contained only 18 ppm cyclododecanone oxime in the laurinolactam. A total amount of 0.22% laurinolactam had been converted into ω-aminododecanoic acid.

The examples clearly show that a ketoxime or aldoxime-containing amide mixture can be converted to a mixture almost entirely free of oxime after a hydrolysis reaction, while converted amine may optionally be recovered again in the same amount.

What is claimed is:

1. A process for treating a ketoxime or aldoxime-containing amide mixture obtained by a Beckmann rearrangement of a ketoxime or aldoxime comprising the steps of
   subjecting the ketoxime or aldoxime-contained amide mixture to a hydrolysis reaction in an aqueous medium under conditions sufficient to change the ketoximes or aldoximes to ketones or aldehydes respectively thus making the amide mixture substantially free of ketoximes or aldoximes;
   separating off the ketones or aldehydes produced by the hydrolysis reaction; and
   subjecting said ketones or aldehydes to an oximation reaction.

2. The process according to claim 1, wherein the hydrolysis reaction is conducted in the presence of a strong mineral or organic acid at a pH from 0 to 4.

3. The process according to claim 2, wherein the pH is from 1.5 to 2.5.

4. The process according to claim 2, wherein the strong mineral or organic acid is selected from the group consisting of sulphuric acid, phosphoric acid, hydrochloric acid, nitric acid, trifluoro acetic acid, p-toluene sulphonic acid, and benzene sulphonic acid.

5. The process according to claim 1, wherein the hydrolysis reaction is conducted in the presence of a heterogeneous catalyst.

6. The process according to claim 5, wherein the heterogeneous catalyst is an acid cation exchanger.

7. The process according to claim 5, wherein the heterogeneous catalyst is phosphoric acid absorbed on carbon black.

8. The process according to claim 1, wherein the hydrolysis reaction takes place at a temperature of from 50° C. to 150° C.

9. The process according to claim 5, wherein the hydrolysis reaction takes place at a temperature of from 80° C. to 120° C.

10. The process according to claim 9, wherein the non-amide products are separated off from amide products by distillation.

11. The process according to claim 1, wherein the ketoxime or aldoxime subjected to a Beckmann rearrangement is selected from the group consisting of acetone oxime, acetaldoxime, benzaldoxime, propanal oxime, butanal oxime, butanone oxime, butene-1-one oxime, cyclopropanone oxime, cyclohexanone oxime, cyclooctanone oxime, cyclododecanone oxime, cyclopentanone oxime, cyclododecenone oxime, 2-phenylcyclohexanone oxime, and cyclohexenone oxime.

12. The process according to claim 1, wherein the ketoxime or aldoxime-containing amide mixture is obtained by a heterogeneously catalytic Beckmann rearrangement.

13. The process according to claim 1, wherein the hydrolysis reaction is carried out batchwise.

14. The process according to claim 1, wherein the hydrolysis reaction is carried out in a continuous process.

* * * * *